United States Patent
Siemer et al.

(10) Patent No.: US 9,586,906 B2
(45) Date of Patent: *Mar. 7, 2017

(54) METHOD OF WORKING UP MIXTURES COMPRISING IMIDAZOLIUM SALTS

(75) Inventors: Michael Siemer, Mannheim (DE); Matthias Maase, Mendham, NJ (US); Ingo Richter, Schwetzingen (DE)

(73) Assignee: BASF SE, Ludwigshafen (DE)

( * ) Notice: Subject to any disclaimer, the term of this patent is extended or adjusted under 35 U.S.C. 154(b) by 1560 days.

This patent is subject to a terminal disclaimer.

(21) Appl. No.: 12/747,702

(22) PCT Filed: Dec. 8, 2008

(86) PCT No.: PCT/EP2008/067025
§ 371 (c)(1),
(2), (4) Date: Jun. 11, 2010

(87) PCT Pub. No.: WO2009/074538
PCT Pub. Date: Jun. 18, 2009

(65) Prior Publication Data
US 2010/0283003 A1    Nov. 11, 2010

(30) Foreign Application Priority Data
Dec. 12, 2007 (EP) ..................................... 07122977

(51) Int. Cl.
*C07D 233/58* (2006.01)

(52) U.S. Cl.
CPC .................................. *C07D 233/58* (2013.01)

(58) Field of Classification Search
CPC .................................................. C07D 233/58
See application file for complete search history.

(56) References Cited

U.S. PATENT DOCUMENTS

| | | | |
|---|---|---|---|
| 5,077,414 A | 12/1991 | Arduengo, III | |
| 5,112,819 A * | 5/1992 | Ross et al. | ............... 514/217.09 |
| 2004/0188350 A1 | 9/2004 | Beste et al. | |
| 2006/0149074 A1 | 7/2006 | Maase et al. | |
| 2008/0251759 A1 | 10/2008 | Kalb et al. | |
| 2010/0137643 A1 | 6/2010 | Tishkov et al. | |

FOREIGN PATENT DOCUMENTS

| | | | |
|---|---|---|---|
| DE | 10 2004 058 907 | 6/2006 | |
| EP | 1 470 846 | 10/2004 | |
| WO | 91 14678 | 10/1991 | |
| WO | WO0294883 | * 1/2002 | ................ 548/335.1 |
| WO | 2005 019183 | 3/2005 | |
| WO | 2005 021484 | 3/2005 | |

OTHER PUBLICATIONS

Schmir, Gaston L. Oxidative Degradation of Imidazoles by Bromine of N-Bromosuccinimide. Biochemistry. 4(3) (1965), 533-538.*
Translation of DE102004043632, accessed online Dec. 17, 2012, URL:http://translationportal.epo.org/emtp/translate/?ACTION=description-retrieval&COUNTRY=DE&ENGINE=google&FORMAT=docdb&KIND=A1&LOCALE=en_EP&NUMBER=102004043632&OPS=ops.epo.org&SRCLANG=de&TRGLANG=en, pp. 1-45.*
U.S. Appl. No. 12/747,372, filed Jun. 10, 2010, Degen, et al.
U.S. Appl. No. 13/511,051, filed May 21, 2012, Neu, et al.

* cited by examiner

*Primary Examiner* — Samantha Shterengarts
(74) *Attorney, Agent, or Firm* — Oblon, McClelland, Maier & Neustadt, L.L.P.

(57) ABSTRACT

Method of lightening the color of mixtures comprising imidazolium salts or imidazoles, wherein the mixtures are treated with an oxidant.

3 Claims, No Drawings

METHOD OF WORKING UP MIXTURES COMPRISING IMIDAZOLIUM SALTS

This application is a 371 of PCT/EP2008/067025 filed Dec. 8, 2008.

The invention relates to a method of lightening the color of mixtures comprising imidazolium salts or imidazoles, wherein the mixtures are treated with an oxidant.

Imidazolium salts have great practical importance as ionic liquids. For the purposes of the present invention, the term ionic liquids refers to salts having a melting point of less than 200° C., in particular salts which are liquid at room temperature.

Ionic liquids, in particular imidazolium salts, are suitable, for example, as solvents in many industrial applications, e.g. for the dissolution of cellulose.

It is therefore desirable to have very simple and inexpensive processes for preparing such imidazolium salts of very high purity and quality.

WO 91/14678 describes a single-stage process for preparing imidazolium salts from an α-dicarbonyl compound, an aldehyde, an amine and an acid (Arduengo process).

This process generally results in a dark to black mixture which comprises the desired imidazolium salts. The color of the mixture is obviously attributable to the presence of by-products.

A multistage process is described, for example, in WO 2005/021484. In this process, a monosubstituted 1-imidazole is first prepared. This 1-imidazole can be separated off by distillation from the dark mixture obtained. Only then is the formation of the disubstituted 1,3-imidazolium salt carried out by reaction with a dialkyl carbonate (carbonate process). It would be advantageous for the process step of isolation of the 1-imidazole to be able to be dispensed with.

It is therefore an object of the present invention to provide a very simple method of improving the preparation of mixtures comprising imidazolium salts. The mixtures should have satisfactory optical and use properties and should be suitable, if possible without further work-up or without isolation of the 1,3-disubstituted imidazoles, for industrial applications, e.g. as solvent for cellulose.

We have accordingly found the method defined at the outset.

Regarding the Mixtures

Mixtures obtained in the preparation of imidazolium salts or imidazoles from carbonyl compounds and amines and, if appropriate, further compounds are preferably used in the method of the invention. In particular, these are mixtures which comprise N,N-disubstituted imidazolium salts or an N-substituted imidazole.

They can be, for example, mixtures which have been obtained by reaction of an α-dicarbonyl compound, an aldehyde, at least one amine and an acid to form the imidazolium salt and, if appropriate, subsequent replacement of the anion (Arduengo process).

The mixtures can also be ones which are obtained by reaction of an α-dicarbonyl compound, an aldehyde, an amine and ammonia to form the monosubstituted imidazole, subsequent reaction with a dialkyl carbonate to give the 1,3-disubstituted imidazolium salt and, if appropriate, subsequent replacement of the anion (carbonate process). In general, the monosubstituted imidazole obtained after the first step has hitherto been separated off from the colored mixture comprising by-products. This separation is no longer necessary when the oxidation according to the invention is employed. The oxidation according to the invention can be carried out after the first step using the mixture which comprises the monosubstituted imidazole or else after the 2nd step using the mixture comprising the disubstituted imidazole.

In both the abovementioned processes, the oxidation can be carried out before or after any subsequent anion exchange. The oxidation is preferably carried out before an anion exchange, should one be intended.

Particular preference is given to using mixtures comprising 1,3-disubstituted imidazolium salts of the formula I

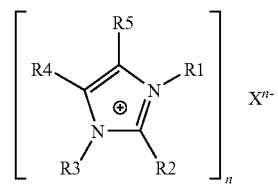

where
R1 and R3 are each, independently of one another, an organic radical having from 1 to 20 carbon atoms,
R2, R4 and R5 are each, independently of one another, an H atom or an organic radical having from 1 to 20 carbon atoms,
X is an anion and
n is 1, 2 or 3.

Such mixtures are, as indicated above, obtained by the Arduengo process or after the second step of the carbonate process.

It is likewise possible to use mixtures which comprise monosubstituted imidazoles of the formula II,

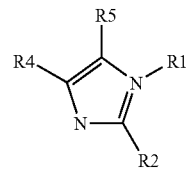

where
R1 is an organic radical having from 1 to 20 carbon atoms,
R2, R4 and R5 are each, independently of one another, an H atom or an organic radical having from 1 to 20 carbon atoms.

These mixtures are obtained, in particular, after the first step of the carbonate process, as indicated above.

The statements made below apply both to compounds of the formula I and to those of the formula II, with all statements regarding R3, X and n applying only to formula I.

Preference is given to R1 and R3 each being, independently of one another, an organic radical having from 1 to 10 carbon atoms. The organic radical can also comprise further heteroatoms, in particular oxygen atoms, for example hydroxyl groups, ether groups, ester groups or carbonyl groups.

In particular, R1 and R3 are each a hydrocarbon radical which may in each case comprise hydroxyl groups, ether groups, ester groups or carbonyl groups in addition to carbon and hydrogen.

Particular preference is given to R1 and R3 each being, independently of one another, a hydrocarbon radical having from 1 to 20 carbon atoms, in particular from 1 to 10 carbon atoms, which does not comprise any other heteroatoms, e.g. oxygen or nitrogen. The hydrocarbon radical can be aliphatic (with the term aliphatic including unsaturated aliphatic groups) or aromatic or comprise both aromatic and aliphatic groups. R1 and R2 are preferably each an aliphatic hydrocarbon radical.

Hydrocarbon radicals which may be mentioned are, for example, the phenyl group, benzyl group, a phenyl or benzyl group bearing one or more C1-C4-alkyl groups as substituents, alkyl groups and alkenyl groups, in particular the allyl group.

Very particular preference is given to R1 and R3 each being a C1-C10-alkyl group. As alkyl group, particular preference is given to a C1-C6-alkyl group, and in a particular embodiment the alkyl group is a C1-C4-alkyl group.

Very particular preference is given to R1 and R3 each being, independently of one another, a methyl, ethyl, n-propyl, isopropyl, n-butyl, sec-butyl or tert-butyl group, with the methyl, ethyl, n-propyl and n-butyl groups being of particular importance.

In a preferred embodiment, R1 and R3 in formula I are each the same organic radical, so that the imidazolium salts of the formula I are in particular symmetrical, disubstituted imidazolium salts.

In an embodiment which is likewise preferred, the imidazolium salts of the formula I are mixtures of imidazolium salts having different radicals R1 and R3. Such mixtures can be obtained by use of different amines, e.g. in the case of primary amines ones having different alkyl groups. The mixture obtained then comprises both imidazolium salts in which R1 and R3 are identical and imidazolium salts in which R1 and R3 are different.

In a particular embodiment, the substituents in the ammonium salts of the formula I have the following meanings:
R1 and R3 are each a methyl group,
R1 and R3 are each an ethyl group,
R1 is a methyl group and R3 is an ethyl group,
R1 is a methyl group and R3 is an n-propyl group,
R1 is a methyl group and R3 is an n-butyl group,
R1 is a methyl group and R3 is an allyl group,
R1 is an ethyl group and R3 is an allyl group,
R1 is a methyl group and R3 is a benzyl group,
R1 is an ethyl group and R3 is a benzyl group.

R2, R4 and R5 are each, independently of one another, an H atom or an organic radical having from 1 to 20 carbon atoms, where R4 and R5 can also together form an aliphatic or aromatic ring. The organic radical can also comprise heteroatoms such as nitrogen or oxygen in addition to carbon and hydrogen; it can preferably comprise oxygen, in particular in the form of hydroxyl groups, ester groups, ether groups or carbonyl groups.

In particular, R2, R4 and R5 are each, independently of one another, an H atom or a hydrocarbon radical which can in each case comprise hydroxyl groups, ether groups, ester groups or carbonyl groups in addition to carbon and hydrogen.

Preference is given to R2, R4 and R5 each being, independently of one another, a hydrogen atom or a hydrocarbon radical which has from 1 to 20 carbon atoms, in particular from 1 to 10 carbon atoms, and does not comprise any other heteroatoms, e.g. oxygen or nitrogen. The hydrocarbon radical can be aliphatic (with the term aliphatic also including unsaturated aliphatic groups) or aromatic or comprise both aromatic and aliphatic groups, where R4 and R5 can also form an aromatic or aliphatic hydrocarbon ring which may optionally be substituted by further aromatic or aliphatic hydrocarbon groups (the number of carbon atoms of the optionally substituted hydrocarbon ring including the substituents can preferably be not more than 40, in particular not more than 20, particularly preferably not more than 15 or not more than 10).

Hydrocarbon radicals which may be mentioned are, for example, the phenyl group, a benzyl group, a phenyl or benzyl group bearing one or more C1-C4-alkyl groups as substituents, alkyl groups, alkenyl groups and, if R4 and R5 form a ring, an aromatic 5- or 6-membered ring, viz. a cyclohexene or cyclopentene, formed by R4 and R5, with these ring systems being able to be substituted, in particular, by one or more C1-C10-, in particular C1-C4-alkyl groups. Aliphatic hydrocarbon radicals are particularly preferred as hydrocarbon radical.

Particular preference is given to R2, R4 and R5 each being, independently of one another, an H atom, a C1-C8-alkyl group or a C1-C8-alkenyl group, e.g. an allyl group.

Very particular preference is given to R2, R4 and R5 each being, independently of one another, an H atom, a methyl, ethyl, n-propyl, isopropyl, n-butyl, sec-butyl or tert-butyl group, with the methyl, ethyl, n-propyl ad n-butyl groups being of particular importance. In a particular embodiment, R2 is, independently of the other radicals R4 and R5 and the other radicals R1 and R3, an H atom. Imidazolium salts of the formula I in which R2 is an H atom are particularly advantageous for the purposes of the present invention since they have good solubility in epoxy compounds and a high effectiveness as latent catalyst. In a particular embodiment, R2 is an H atom when the anion is an acetate.

In a Particular Embodiment,
R2, R4 and R5 are each an H atom,
R2 is an H atom or a C1-C4-alkyl group and R4, R5 are each an H atom or a C1-C4-alkyl group.

Specific examples of cations of the compounds of the formula I are:
1-butyl-3-methylimidazolium (R1=butyl, R3=methyl)
1-butyl-3-ethylimidazolium (R1=butyl, R3=ethyl)
1,3-dimethylimidazolium (R1=methyl, R3=methyl)
1,3-diethylimidazolium (R1=ethyl, R3=ethyl)
1-ethyl-3-methylimidazolium (R1=ethyl, R3=methyl)
1-ethyl-2,3-dimethylimidazolium (R1=ethyl, R2=methyl, R3=methyl).

As imidazole compounds of the formula II, mention may be made of:
1-methylimidazole
1-ethylimidazole
1-propylimidazole
1-butylimidazole.

In formula I, n is 1, 2 or 3; accordingly, the anion has one, two or three negative charges and one, two or three imidazolium cations are correspondingly present in the salt.

n is preferably 1 or 2, particularly preferably 1; the anion is therefore particularly preferably monovalent.

In formula I, X is preferably the anion of a hydrogen acid.

As suitable anions $X^-$, mention may be made of, for example, compounds having one or more carboxylate groups (carboxylates for short).

As such carboxylates, mention may be made of, in particular, organic compounds having from 1 to 20 carbon atoms and comprising one or two carboxylate groups, preferably one carboxylate group.

Both aliphatic and aromatic compounds are possible, with aromatic compounds being compounds comprising aromatic groups. Particular preference is given to aliphatic or aromatic compounds which, apart from the oxygen atoms of the carboxylate group, comprise no further heteroatoms or at most one or two hydroxyl groups, carbonyl groups or ether groups. Very particular preference is given to aliphatic or aromatic compounds which do not comprise any further heteroatoms apart from the oxygen atoms of the carboxylate group.

As compounds having two carboxylate groups, mention may be made of, for example, the anions of phthalic acid, of isophthalic acid, of C2-C6-dicarboxylic acids, e.g. oxalic acid, malonic acid, succinic acid, glutaric acid, adipic acid.

As compounds having one carboxylate group, mention may be made of the anions of aromatic, aliphatic, saturated or unsaturated C1-C20-carboxylic acids, in particular alkanecarboxylic acids, alkenecarboxylic acids, alkynecarboxylic acids, alkadienecarboxylic acids, alkatrienecarboxylic acids, hydroxycarboxylic acids or ketocarboxylic acids. Suitable alkanecarboxylic acids, alkenecarboxylic acids and alkadienecarboxylic acids are also known as fatty acids.

Particular mention may be made of the anions of formic acid (formate) or acetic acid (acetate). A very particularly preferred anion X is the acetate anion.

Further anions which are of importance, in particular in the Arduengo method by selection of the corresponding acid as starting compound, are, for example, halides, in particular chloride, borates, alkylsulfonates, in particular methylsulfonate, and thiocyanate (rhodanide).

The preparation of the mixtures of the appropriate starting compounds (α-dicarbonyl compound, aldehyde, an amine and the hydrogen acid of the anion X) is known and is carried out, for example, as described in WO 91/14678 (Arduengo method) or WO 2005/021484 (carbonate method). The α-dicarbonyl compound is preferably a compound of the formula

where R4 and R5 are as defined above.

Particular preference is given to glyoxal.

The aldehyde is, in particular, an aldehyde of the formula R2-CHO, where R2 is as defined above. Particular preference is given to formaldehyde; the formaldehyde can also be used in the form of compounds which release formaldehyde, e.g. paraformaldehyde or trioxane.

The amines are, in particular, primary amines of the type R—$NH^2$. The radical R corresponds to the radicals R1 and R3 of the imidazolium salts obtained. When a defined primary amine is used, an imidazolium salt in which the radicals R1 and R3 are identical is obtained. If a mixture of amines (e.g. a mixture of R'—$NH^2$ and R"—$NH^2$) is used, the result is a mixture of imidazolium salts (mixture of salts in which R1 and R3=R', R1 and R3=R" and salts in which R1=R' and R3=R").

The hydrogen acid is the desired hydrogen acid of the anion X, preferably an alkanecarboxylic acid, particularly preferably acetic acid.

Further Constituents of the Mixture

The mixtures can comprise solvents. Insofar as solvents are comprised, preference is given to water, a solvent which is miscible with water or a mixture thereof. As solvents which are miscible with water, mention may be made of, in particular, protic solvents, preferably aliphatic alcohols or ethers having not more than 4 carbon atoms, e.g. methanol, ethanol, methyl ethyl ether, tetrahydrofuran. Suitable protic solvents are miscible with water in any ratio (at 1 bar, 21° C.). A particularly preferred solvent is water.

The method of the invention can be carried out using solvent-comprising mixtures or solvent-free mixtures.

The mixtures have a dark color which is attributable to by-products formed in the process for preparing the imidazolium salts or imidazoles (Arduengo or carbonate method).

Regarding the Oxidation

According to the invention, the mixtures are treated with an oxidant.

Suitable oxidants are known to those skilled in the art. Oxidants are compounds having a high affinity for electrons (electrophilicity). Compounds which are strongly electrophilic and thus suitable as oxidants are, for example, oxygen and oxygen-comprising per compounds, in particular hydrogen peroxide, metal peroxides or organic peroxides, e.g. sodium persulfate or tert-butyl hydroperoxide, inorganic and organic peracids, e.g. periodic acid or percarboxylic acids, and also other compounds such as sulfur or metal compounds having high oxidation states (e.g. iron(III) compounds, manganese dioxide, potassium permanganate, chromic acid, chromic anhydride, lead dioxide or lead tetraacetate).

The oxidant is preferably oxygen or a peroxide or peracid, with particular preference being given to hydrogen peroxide.

The oxidant can, for example, be gaseous or liquid. Possible oxidants are, in particular, gaseous oxygen which is brought into contact with the reaction mixture in a suitable way, e.g. by means of pressure and/or passing it into the liquid below the surface of the liquid.

Further possible oxidants are, in particular, liquid oxidants, in particular oxidants which are dissolved in suitable solvents which are miscible with the reaction mixture. Possible solvents are, in particular, water, a solvent which is miscible with water or a mixture thereof, corresponding to the above solvents for the mixture.

Preference is given to gaseous oxygen and especially hydrogen peroxide, preferably in the form of solutions as described above, in particular as a 10-40% strength by weight solution.

The amount of oxidant is chosen according to requirements; per 1 mol of imidazolium salt or imidazole (on the basis of the amount theoretically obtained from the reaction batch) it is possible to use, for example, at least 0.01 mol or at least 0.1 mol, preferably at least 0.5 mol, of oxidant; the total amount of oxidant can be, for example, from 0.01 to 20 mol, preferably from 0.1 to 20 mol or from 0.5 to 10 mol.

The oxidation can, for example, be carried out at temperatures of from 20 to 100° C., in particular from 50 to 90° C., under atmospheric pressure until lightening of the mixture occurs.

A work-up or partial work-up of the reaction mixture can be carried out before or after the oxidation. In particular, the further work-up, if desired, e.g. removal of the solvent, is carried out only after the oxidation.

The mixtures obtained have a significantly lighter color than has hitherto been usual. Unexpectedly, the oxidation alters the nature of the by-products so that the discoloration is significantly reduced. In the preparation by the carbonate method, isolation of the imidazole (and associated therewith, purification) after the first step is no longer necessary. The mixtures obtained are directly suitable for further uses, e.g. as solvents, in particular as solvents for cellulose.

EXAMPLES

Example 1

Preparation of 1,3-diethylimidazolium acetate (EEIM acetate)

Reaction Equation:

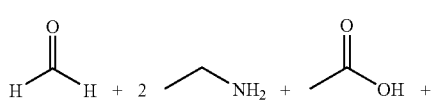

-continued

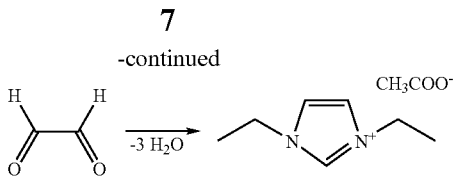

Stirring rate: Reaction vessel: 350 rpm
Apparatus:
  6 l four-neck flask, semicircular Teflon stirrer, thermometer, condenser, dropping funnel
Batch:

| | | Substance | |
|---|---|---|---|
| 252.1 g | 8.15 mol | of paraformaldehyde 97% strength | and |
| 325 g | 18.04 mol | of water | are placed in a reaction vessel |
| 1048.7 g | 16.27 mol | of ethylamine 70% strength in water | are added dropwise |
| 488.9 g | 8.15 mol | of glacial acetic acid | are added dropwise |
| 1181.4 g | 8.15 mol | of glyoxal 40% in water | are added dropwise |

| Time | Temperature | |
|---|---|---|
| 8:55 | 10° C. | Paraformaldehyde and water are placed in a reaction vessel, White suspension, ethylamine added dropwise at 20-30° C., exothermic reaction, cooling in an ice bath |
| 9:35 | 23° C. | After half of the amine has been added dropwise, the evolution of heat decreases, a clear solution is obtained |
| 9:50 | 23° C. | End of addition, mixture is stirred at RT for 30 min |
| 10:35 | 25° C. | Glacial acetic acid added dropwise at 20-30° C., exothermic reaction, cooling in an ice bath, white mist is formed |
| 11:10 | 25° C. | End of addition, two clear phases, mixture is stirred at RT for 20 min |
| 11:30 | 21° C. | Glyoxal added dropwise at 20-35° C., the mixture becomes a single phase and darkens from yellow to blackish brown |
| 12:00 | 22° C. | End of addition, mixture stirred overnight at RT |

Work-Up:

The blackish brown product mixture obtained was heated to 70° C. (pH 6.68) and 1.5 kg of hydrogen peroxide 30% strength were added dropwise at 70-80° C. over a period of about 1 hour. After the addition was complete, lightening of the color was observed (pH 6.33). The mixture was stirred at 80° C. for another 4 hours (no evolution of gas); a further lightening of the color occurred (light-orange pH 6.08).

The speed of the stirrer was increased to 480 rpm and about 375 g of NaOH 40% strength were added dropwise over a period of about 1.5 hours to neutralize excess acid. The temperature stayed at 65° C. without further heating, and the pH rose to 9.5 with very vigorous evolution of gas (decomposition of hydrogen peroxide, $H_2O_2$). The temperature rose to 95° C., at pH 10.3. The addition was stopped and the mixture was stirred overnight at room temperature (RT) (lightening to yellow).

The product mixture (pH 11.2) was evaporated on a rotary evaporator, 1.5 kg of acetonitrile were added and the mixture was stirred overnight. The sodium salt of the excess acid precipitates and is separated off. The mixture was then evaporated on a rotary evaporator.

A total of 1444.14 gram of product (EEIM acetate, $^1$H-NMR) were obtained.

Examples 2 to 12

Various ionic liquids were stored at 110° C. in a drying oven for 72 hours and subsequently admixed with 0.5 gram of hydrogen peroxide ($H_2O_2$) and then assessed visually and the color number was determined by the Gardner method (the higher the color number, the darker the material).

| Imidazolium salt | Gardner color number before addition of $H_2O_2$ | Visual assessment after addition | Color number after addition | $H_2O_2$ content |
|---|---|---|---|---|
| HMIM-HSO$^4$ | | lighter | | 0.09% by weight |
| EMIM-EtOSO$^3$ | | unchanged | | |
| EMIM-HSO$^4$ | 11.1 | lighter | 10.1 | 0.83% by weight |
| EMIM-MeSO$^3$ | 11.4 | lighter | 5.1 | 0.11% by weight |
| EMIM-SCN | 14.4 | | 14.6 | 59 ppm |
| BMIM acetate | 13.9 | lighter | 8.3 | 0.5% by weight |
| BMIM chloride | | unchanged | | |
| BMIM-$H_2SO_4$ | 5.6 | lighter | 4.4 | 0.79% by weight |
| BMIM-MeSO$_3$ | 8.9 | lighter | 6.2 | 0.48% by weight |
| BMIM-MeOSO$_3$ | | unchanged | | |
| BMIM-SCN | 8.4 | turbid | 15.2 | 50 ppm |

HMIM, EMIM, BMIM are imidazolium salts of the formula I above with radicals R1 and R3 as follows:
HMIM: R1=H and R3=methyl
EMIM: R1=ethyl and R3=methyl
BMIM: R1=butyl and R3=methyl

The invention claimed is:
1. A method of lightening the color of a mixture comprising an imidazolium salt, comprising treating the mixture with an oxidant, wherein prior to said treating said mixture is a colored mixture, and wherein said treating lightens the color of said colored mixture.

2. A method of lightening the color of a mixture comprising an imidazolium salt, comprising treating the mixture with an oxidant wherein the mixture comprises a 1,3-disubstituted imidazolium salt of the formula I:

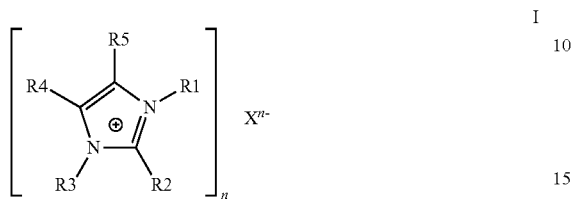

where
R1 and R3 are each, independently of one another, an organic radical having from 1 to 20 carbon atoms,
R2, R4 and R5 are each, independently of one another, an H atom or an organic radical having from 1 to 20 carbon atoms,
X is an anion and
n is 1, 2 or 3; and, wherein prior to said treating said mixture is a colored mixture, and wherein said treating lightens the color of said colored mixture.

3. The method according to claim 2, wherein said colored mixture comprises 1,3-diethylimidazolium acetate.

* * * * *